(12) United States Patent
Strauss (10) Patent No.: US 9,988,686 B2
(45) Date of Patent: Jun. 5, 2018

(54) STIMULUS-SENSITIVE MICROPARTICLES AND METHODS OF USE

(71) Applicant: William M. Strauss, Westlake Village, CA (US)

(72) Inventor: William M. Strauss, Westlake Village, CA (US)

(73) Assignee: Cynvenio Biosystems, Inc., Westlake, CA (US)

( * ) Notice: Subject to any disclaimer, the term of this patent is extended or adjusted under 35 U.S.C. 154(b) by 166 days.

(21) Appl. No.: 14/429,901

(22) PCT Filed: Sep. 27, 2013

(86) PCT No.: PCT/US2013/062373
§ 371 (c)(1),
(2) Date: Jun. 19, 2015

(87) PCT Pub. No.: WO2014/052875
PCT Pub. Date: Apr. 3, 2014

(65) Prior Publication Data
US 2015/0211072 A1    Jul. 30, 2015

Related U.S. Application Data

(60) Provisional application No. 61/706,126, filed on Sep. 27, 2012.

(51) Int. Cl.
| | | |
|---|---|---|
| C12Q 1/68 | (2018.01) | |
| G01N 33/545 | (2006.01) | |
| G01N 33/574 | (2006.01) | |
| C07H 21/02 | (2006.01) | |

(52) U.S. Cl.
CPC ......... *C12Q 1/6886* (2013.01); *G01N 33/545* (2013.01); *G01N 33/57484* (2013.01); *G01N 33/57492* (2013.01); *C12Q 2600/156* (2013.01); *C12Q 2600/166* (2013.01); *G01N 2458/00* (2013.01); *G01N 2458/10* (2013.01); *G01N 2496/80* (2013.01)

(58) Field of Classification Search
CPC ............ C12Q 1/6886; C12Q 2600/156; C12Q 2600/166; G01N 2458/00; G01N 2458/10; G01N 2496/80; G01N 33/545; G01N 33/57484; G01N 33/57492
See application file for complete search history.

(56) References Cited

U.S. PATENT DOCUMENTS

| | | | |
|---|---|---|---|
| 5,783,567 A | 7/1998 | Hedley et al. | |
| 6,828,357 B1* | 12/2004 | Martin | A61K 9/1647 523/124 |
| 8,071,395 B2 | 12/2011 | Davis et al. | |
| 2001/0018192 A1 | 8/2001 | Terstappen et al. | |
| 2002/0182258 A1 | 12/2002 | Lunsford et al. | |
| 2004/0009941 A1 | 1/2004 | Johnson et al. | |
| 2004/0101822 A1 | 5/2004 | Wiesner et al. | |
| 2009/0220587 A1* | 9/2009 | Allon | A61K 9/1272 424/450 |
| 2011/0268810 A1* | 11/2011 | Saltzman | C12N 15/88 424/499 |
| 2012/0094275 A1 | 4/2012 | Rao et al. | |

FOREIGN PATENT DOCUMENTS

| | | |
|---|---|---|
| CN | 1742094 A | 3/2006 |
| CN | 101357315 A | 2/2009 |
| EP | 0341391 A1 | 11/1989 |
| EP | 1335706 B1 | 8/2003 |
| RU | 2236868 | 9/2004 |
| WO | 93/10226 | 5/1993 |
| WO | WO 94/23699 | * 10/1994 |
| WO | 96/00295 | 1/1996 |

OTHER PUBLICATIONS

Rehm, B.H.A., Curr. Issues Mol. Biol., vol. 9, pp. 41-62 (2007).*
Biotek Tech Note "Excitation and Emission of Green Fluorescent Proteins", pp. 1-3 (2006).*
Avgoustiakis, K., Encyclopedia of Biomat. Biomed. Eng., pp. 1-11 (2005).*
Makadia, H. et al., Polymers, vol. 3, pp. 1377-1397 (2011).*
Woodruff, M.A. et al., Polymer Sci., vol. 35, pp. 1217-1256 (2010).*
CN patent application No. 201380061891.5, Office Action dated Oct. 28, 2016.
EP patent application No. 13841433.9, Supplemental European Search Report dated Jul. 11, 2016.
WO patent application No. PCT/US2013/062373, International Search Report and Written Opinion dated Sep. 27, 2013.
WO patent application No. PCT/US2013/062373, International Preliminary Report on Patentability dated Apr. 9, 2015.
Allard, W. Jeffrey et al., "Tumor cells circulate in the peripheral blood of all major carcinomas but not in healthy subjects or patients with nonmalignant diseases," *Clinical Cancer Research* vol. 10, 6897-6904, Oct. 15, 2004.
Baras, B. et al., "Influence of various technological parameters on the preparation of spray-dried poly(ε-caprolactone) microparticles containing a model antigen," *J. Microencapsulation*, 2000, vol. 17, No. 4, 485-498, Sep. 5, 1999.
Chandler, Darrell P. et al., "Continuous spore disruption using radially focused, high-frequency ultrasound," *Anal. Chem.* 2001, 73, 3784-3789, Aug. 1, 2001.
Quintero-Betancourt, W. et al., "Assessment of methods for detection of infectious *Cryptosporidium* oocysts and *Giardia* cysts in reclaimed effluents," *Applied and Environmental Microbiology*, vol. 69, No. 9, Sep. 2003, p. 5380-5388.
Warnecke, M. et al., "Evaluation of an internal positive control for *Cryptosporidium* and *Giardia* testing in water samples," *Letters in Applied Microbiology* 2003, 37, 244-248, Jun. 1, 2003.

(Continued)

*Primary Examiner* — Teresa E Strzelecka
(74) *Attorney, Agent, or Firm* — Weaver Austin Villeneuve & Sampson LLP (57) ABSTRACT

Provided are stimulus-sensitive microparticles and their use, e.g., in tracking the efficiency of recovery of a rare cell population (e.g., circulating tumor cells) from a mixture of cells; and in supplying control nucleic acids to index a molecular assay independent of the rare cell selection steps.

25 Claims, 2 Drawing Sheets

(56) References Cited

OTHER PUBLICATIONS

Huang, et al., "Molecular Weight Dependence of the Melting Behavior of Poly (ε-Caprolactone)" *Chinese Journal of Polymer Science* 20(1):45-51, 2002.

* cited by examiner

STIMULUS-SENSITIVE MICROPARTICLES AND METHODS OF USE

CROSS-REFERENCE TO RELATED APPLICATIONS

The present application is a U.S. National Phase filing under 35 U.S.C. § 371 of International Application No. PCT/US2013/062373, filed on Sep. 27, 2013, which claims the benefit under 35 U.S.C. § 119(e) of U.S. Provisional Application No. 61/706,126, filed on Sep. 27, 2012, which are hereby incorporated herein by reference in their entireties for all purposes.

FIELD OF THE INVENTION

Provided are stimulus-sensitive microparticles and their use, e.g., in tracking the efficiency of recovery of a rare cell population (e.g., circulating tumor cells) from a mixture of cells; and in supplying control nucleic acids to index a molecular assay independent of the rare cell selection steps.

BACKGROUND OF THE INVENTION

Solid tissue cancers start to grow at a primary site. As the disease progresses, metastases arise at distant locations. These metastatic events accelerate the disease and eventually lead to death. Cells or fragments of cells leave the primary site as part of the metastatic process. The process of metastasis is complex. Part of the metastatic process involves rare circulating tumor cells (CTC). That these CTC are not a monolithic population within a given patient is becoming clear. Fractionation of the CTC's within a patient is essential to understand the mutations responsible for the cancer afflicting the patient. Purification and isolation of these rare tumor cells (or cell derived events) is required to define oncogenic mutations in patient blood. Many cells and cell fragments exist in whole blood that do not contain mutations, thus in order to isolate the useful mutation bearing cells, a purification strategy is required.

In order to measure mutations in the DNA genome of a rare cell population, e.g., circulating tumor cells (CTC), from a mixture of cells, by any technology, DNA of sufficient quantity and quality is required. Typically from 2 to 4 ml of whole blood, one can expect 2 to 10 CTCs to be recovered. This number of cells must be processed with excellent recovery to ensure that mutation bearing chromosomes are not lost during processing.

SUMMARY

The embodiments disclosed herein are based, in part, on the discovery of thermolabile microspheres and their use in tracking the efficiency of isolation of genomic DNA from cells of a rare cell population that are isolated from a mixture of cells (e.g., from a biological sample). The thermolabile microspheres and methods for tracking described herein provide a multistep process internal control capability that allows for calibration of performance, e.g., at the level of cell isolation and again at the level of genomic DNA isolation.

In one aspect, the invention provides thermolabile microspheres. In some embodiments, the thermolabile microspheres comprise:

i) a thermolabile polymer comprising an inner space and an external surface, wherein the polymer contains a target nucleic acid in the inner space, wherein the polymer comprises a sharp melting point and releases the nucleic acid at a temperature above about 50° C.; and ii) an immunogenic epitope or antigen, or surface or other marker attached to an external surface of the polymer. In some embodiments, the thermolabile microsphere further comprises iii) a detectable label and being detectable while contained within the thermolabile polymer. Optionally, the detectable label is contained in the inner space of the thermolabile microspheres. In some embodiments, the thermolabile polymer is a homopolymer. In some embodiments, the thermolabile polymer comprises a sharp melting point within a temperature range of about 50° C. to about 110° C., e.g., in the range of about 50-60° C. or 55-65° C., e.g., about 50° C., 55° C., 60° C., 65° C., 70° C., 75° C., 80° C., 85° C., 90° C., 95° C., 100° C., 105° C. or 110° C. In some embodiments, the thermolabile polymer comprises a polymer that degrades in aqueous buffer at a temperature above about 50° C., e.g., above about 55° C., above about 60° C. or above about 65° C. In some embodiments, the thermolabile polymer is selected from the group consisting of polycaprolactone (PCL), poly L-lysine (PLL), polystyrene, polymethyl methacrylate (PMMA), Poly Lactic-co-Glycolic Acid (PLGA), polyisopropyl acrylamide, butyl vinyl ether, cis-chlorobutadiene, ethylene adipate, ethylene oxide, ethylene vinyl acetate, ethyl vinyl ether, trans-isoprene, poly (hexene 1), poly(methyl methacrylate), poly(vinyl chloride), propylene oxide, propyl vinyl ether and vinyl acetal. In some embodiments, the thermolabile polymer is biodegradable. In some embodiments, the thermolabile polymer is a biodegradable polyester. In some embodiments, the thermolabile polymer is polycaprolactone (PCL). In some embodiments, the polycaprolactone (PCL) comprises a molecular weight in the range of about Mn 10,000 to about Mn 90,000, e.g., about Mn 10,000-14,000, Mn 45,000, or Mn 70,000-90,000. In some embodiments, the thermolabile polymer is a polyhydroxyalkanoate. In some embodiments, the microsphere has a size in the range of about 10-30 μm, e.g., in the range of about 20-30 μm, e.g., an average or mean diameter of about 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, or 30 μm. In some embodiments, the target nucleic acid is comprised in a DNA plasmid. In some embodiments, the target nucleic acid encodes a non-human DNA sequence or a mutated human DNA sequence or an artificial DNA sequence. In some embodiments, the target nucleic acid encodes a gene selected from plasmid maintenance protein, ccdB and 3',5'-cyclic adenosine monophosphate phosphodiesterase, cpdA. In some embodiments, the immunogenic epitope or antigen, or surface or other marker comprises one or more CTC-associated markers, e.g., Epithelial cell adhesion molecule (Ep-CAM), KRT19, MUC1, CEACAM5, BIRCS, SCGB2A2, and ERBB2. In some embodiments, the immunogenic epitope or antigen, or surface or other marker is selected from biotin, Epithelial cell adhesion molecule (Ep-CAM) and digoxigenin. In some embodiments, the detectable label is a fluorophore. In some embodiments, the fluorophore comprises an excitation peak at about 460 nm and an emission peak at about 500 nm, e.g., FAM. In some embodiments, the fluorophore is selected from the group consisting of a xanthene derivative (e.g., fluorescein, rhodamine, Oregon green, eosin, and Texas red) a cyanine derivative (e.g., cyanine, indocarbocyanine, oxacarbocyanine, thiacarbocyanine, and merocyanine), a naphthalene derivative (e.g., dansyl and prodan derivatives), a coumarin derivative (e.g., hydroxycoumarin, methoxycoumarin and aminocoumarin), an oxadiazole derivative (e.g., pyridyloxazole, nitrobenzoxadiazole and benzoxadiazole), a pyrene derivative (e.g., cascade blue), an oxazine derivative (e.g., Nile red, Nile blue, cresyl violet, oxazine 170), an acridine derivative (e.g., proflavin, acridine orange, acridine yellow), an arylmethine derivative (e.g., auramine, crystal violet, malachite green), and a tetrapyrrole derivative (e.g., porphin, phtalocyanine, bilirubin).

In a further aspect, the invention provides methods of tracking the efficiency of recovery of cells of a rare cell population from a mixture of cells. In some embodiments, the methods comprise:

a) mixing a predetermined number of thermolabile microspheres as described above and herein with a mixture of cells suspected of comprising a cell of a rare cell population, wherein the immunogenic epitope or antigen, or surface or other marker attached to the external surface of microsphere is the same epitope or antigen used to isolate the rare cell population;

b) adding to the mixture of cells comprising the thermolabile microspheres a binding partner that binds to the immunogenic epitope or antigen, or surface or other marker; and c) concurrently isolating binding partner-bound microspheres and cells of the rare cell population from the mixture of cells, wherein the number of microspheres captured is representative of the efficiency of capture of cells in the rare cell population from the mixture of cells; thereby tracking the efficiency of recovery of a rare cell population from a mixture of cells.

In a further aspect, the invention provides methods of tracking the efficiency of recovery of a rare cell population and the efficiency of recovery of genomic DNA from a mixture of cells. In some embodiments, the methods comprise:

a) mixing a predetermined number of thermolabile microspheres as described above and herein with a mixture of cells suspected of comprising a cell of a rare cell population, wherein the immunogenic epitope or antigen, or surface or other marker attached to the external surface of microsphere is the same epitope or antigen used to isolate the rare cell population;

b) adding to the mixture of cells comprising the thermolabile microspheres a binding partner that binds to the immunogenic epitope or antigen, or surface or other marker;

c) concurrently isolating binding partner-bound microspheres and cells of the rare cell population from the mixture of cells, wherein the number of microspheres captured is representative of the efficiency of capture of cells in the rare cell population from the mixture of cells;

d) subjecting the isolated microspheres and isolated cells in the rare cell population to a temperature of at least 50° C., under conditions that concurrently release genomic DNA from the cells and release the target nucleic acid from the microsphere; and e) concurrently amplifying and quantifying the genomic DNA from the isolated cells and the target nucleic acid released from the thermolabile microspheres, wherein the quantity of target nucleic acid amplified is representative of the efficiency of recovery of genomic DNA from the isolated cells of the rare cell population, thereby tracking the efficiency of recovery of the rare cell population and the efficiency of recovery of genomic DNA from the mixture of cells.

In some embodiments, the method further comprise:
prior to d), identifying a number of microspheres isolated during c) by interrogating the detectable label; and
comparing the identified number of microspheres with the predetermined number provided in a). In some embodiments, the cells in the rare cell population are eukaryotic cells or prokaryotic cells. In some embodiments, the rare cell population comprises circulating tumor cells (CTC). In some embodiments, the mixture of cells is in a biological sample from a patient. In some embodiments, the biological sample is whole blood. In some embodiments, the predetermined number of thermolabile microspheres is in the range of about 10 to about 100 microspheres. In some embodiments, the patient is a human. In some embodiments, the binding partner that binds to the immunogenic epitope or antigen, or surface or other marker is an antibody or antibody fragment.

In a further aspect, provided is a stimulus-sensitive microparticle. In some embodiments, the microparticle comprises:

i) a shell comprising an inner space and an external surface, wherein the shell contains one or more reporting molecules in the inner space, wherein the shell releases the one or more reporting molecules upon exposure to a stimulus; and ii) an immunogenic epitope attached to an external surface of the shell. In varying embodiments, the microparticle is spherical. In some embodiments, the microparticle comprises an average diameter in the range of about 1 µm to about 100 µm, e.g., an average diameter in the range of about 1 µm to about 10 µm, e.g., an average diameter in the range of about 10 µm to about 100 µm. In varying embodiments, the stimulus is temperature, pH, irradiation, light and/or contact with an enzyme. In varying embodiments, the shell comprises or is composed of one or more polymers, a unilamellar micelle, a bilamellar micelle, a dendrimer or dendrosome and/or carbon nanotubes. In some embodiments, the shell is comprised of pH-sensitive dendrimers or dendrosomes, liposomes or one or more polymers. In some embodiments, the shell is comprised of temperature-sensitive dendrimers or dendrosomes, liposomes or polymers. In varying embodiments, the shell is comprised of a homopolymer, e.g., a biodegradable polyester. In some embodiments, the homopolymer comprises a sharp melting point and releases the nucleic acid at a temperature above about 50° C. In some embodiments, the homopolymer is selected from the group consisting of polycaprolactone (PCL), poly L-lysine (PLL), polystyrene, polymethyl methacrylate (PMMA), Poly Lactic-co-Glycolic Acid (PLGA), polyisopropyl acrylamide, butyl vinyl ether, cis-chlorobutadiene, ethylene adipate, ethylene oxide, ethylene vinyl acetate, ethyl vinyl ether, trans-isoprene, poly(hexene 1), poly(m-ethyl methacrylate), poly(vinyl chloride), propylene oxide, propyl vinyl ether and vinyl acetal. In some embodiments, the homopolymer is polycaprolactone (PCL). In some embodiments, the shell is comprised of one or more co-polymers. For example, in varying embodiments, the shell comprises N isopropyl acrylamide (NIPAAm), propyl acrylic acid (PAA), and butyl acrylate (BA). In some embodiments, the shell comprises carboxymethyl chitosan (CMCTS) and carboxymethyl chitosan-graft-poly(N,N-diethylacrylamide) (CMCTS-g-PDEA). In some embodiments, the shell comprises trimethyl-chitosan (TMC), poly (ethylene glycol)dimethacrylate (PEGDMA) and methacrylic acid (MAA). In some embodiments, the shell comprises poly(Nisopropylacrylamide) (PNIPAM) and polyethylene glycol (PEG). In some embodiments, the shell comprises poly(methacrylic acid (MAA)-co-ethyleneglycol dimethacrylate (EGDMA) (P(MAA-co-EGDMA) or poly (methacrylic acid (MAA)-co-ethyleneglycol methacrylate (EGMA) (P(MAA-co-EGMA). In some embodimetns, the shell comprises hydrolyzed methacrylated gelatin (HGel-MA), N,N' methylenebisacrylamide and N isopropylacrylamide. In some embodiments, the shell comprises Ca alginate (Ca-ALG), alginate-oligochitosan (ALGOCH) and alginate-oligochitosan-EUDRAGIT® L100-55 (ALG-OCH-EL). In varying embodiments, the shell is comprised of dendrimers or dendrosomes. In some embodiments, the dendrosomes are comprised of hyperbranched polyglycerol, β-cyclodextrin and bi chain polycaprolactone (BPCL). In some embodiments, the shell releases the one or more reporting molecules at a pH below about 7 or above about 8, or at a temperature below about 20° C. or above about 37° C. In some embodiments, the shell is comprised of oleamide derivatives. In varying embodiments, the one or more reporting molecules comprise a target nucleic acid. In some embodiments, the target nucleic acid comprises DNA. In some embodiments, the target nucleic acid is comprised in a DNA plasmid. In some embodiments, the target nucleic acid encodes a non-human DNA sequence or a mutated human DNA sequence or an artificial DNA sequence. In some embodiments, the one or more reporting molecules comprise a detectable label. In varying embodiments, the detectable label is a fluorophore. In varying embodiments, the fluorophore comprises an excitation peak at about 460 nm and an emission peak at about 500 nm. In some embodiments, the immunogenic epitope or antigen is selected from Epithelial cell adhesion molecule (Ep-CAM), digoxigenin, and biotin.

In another aspect, provided are methods of tracking the efficiency of recovery of cells of a rare cell population from a mixture of cells. In some embodiments, the methods comprise:

a) mixing a predetermined number of microparticles as described above and herein with a mixture of cells suspected of comprising a cell of a rare cell population, wherein the immunogenic epitope or antigen attached to the external surface of microparticle is the same epitope used to isolate the rare cell population;

b) adding to the mixture of cells comprising the microparticles a binding partner that binds to the immunogenic epitope;

c) concurrently isolating binding partner-bound microparticles and cells of the rare cell population from the mixture of cells, wherein the number of microparticles captured is representative of the efficiency of capture of cells in the rare cell population from the mixture of cells;

d) subjecting the isolated microparticles and isolated cells in the rare cell population to conditions that concurrently release genomic DNA from the cells and release the one or more reporting molecules from the microparticle; and e) concurrently quantifying the genomic DNA from the isolated cells and the one or more reporting molecules released from the microparticles, wherein the quantity of one or more reporting molecules is representative of the efficiency of recovery of genomic DNA from the isolated cells of the rare cell population, thereby tracking the efficiency of recovery of the rare cell population from the mixture of cells. In some embodiments, the methods further comprise, prior to d), identifying a number of microparticles isolated during c) by interrogating the one or more reporting molecules; and comparing the identified number of microparticles with the predetermined number provided in a). In varying embodiments, the rare cell population comprises eukaryotic cells, e.g., circulating tumor cells (CTC). In varying embodiments, the microparticles comprise a size and shape that approximates or is similar to the cells being tracked, captured, recovered and processed. In varying embodiments, the mixture of cells is in a biological sample from a patient, e.g., whole blood. In some embodiments, the patient is a human. In some embodiments, the predetermined number of microparticles is in the range of about 10 to about 100 microparticles. In some embodiments, the binding partner that binds to the immunogenic epitope or antigen is an antibody or antibody fragment. In some embodiments, the rare cell population comprises prokaryotic cells. In some embodiments, the mixture of cells is in a water sample. In some embodiments, the mixture of cells is in a food sample.

DEFINITIONS

The term "sharp melting point" refers to the transition of a polymer from a crystalline or semi-crystalline phase to a liquid/melt/flow phase over 10 or fewer ° C., e.g., over 9, 8, 7, 6, 5 or fewer ° C. In various embodiments, the polymer comprises monomers of a substantially uniform molecular weight, e.g., a molecular weight distribution of about 10% or less.

The term "rare cell population" refers to a cell population in a sample that is fewer than $1/10^6$ (i.e., one in one million or $10^{-4}$%) of the total cells in the sample, oftentimes fewer than $1/10^7$ (i.e., one in ten million or $10^{-5}$%), or fewer than $1/10^8$ (i.e., one in one hundred million or $10^{-6}$%), or fewer than $1/10^9$ (i.e., one in one billion or $10^{-7}$%). Cells in a rare cell population can be eukaryotic cells or prokaryotic cells. Illustrative example of a rare cell populations include without limitation, e.g., circulating tumor cells (CTC), stem cells, dendritic cells, endothelial progenitor cells, circulating endothelial cells, cancer stem cells, cytokine-secreting cells, antigen-specific T cells, and nucleated fetal erythrocytes. Circulating tumor cells are found in frequencies in the order of 1-10 CTC per mL of whole blood in patients with metastatic disease. For comparison, one milliliter of blood contains a few million white blood cells and a billion red blood cells.

Biological and biochemical terminology: Where specific categories of molecules are discussed, such as nucleic acids or proteins, synthetic forms are included, such as mimetic or isomeric forms of naturally occurring molecules. Unless otherwise indicated, modified versions are similarly encompassed, so long as the desired functional property is maintained. For example, an aptamer selective for a CD34 cell surface protein includes chemical derivatives (e.g., pegylated, creation of a pro-form, derivatized with additional active moieties, such as enzymes, ribozymes, etc.)

The term "biological fluid" denotes the source of the fluid, and includes (but is not limited to) amniotic fluid, aqueous humor, blood and blood plasma (and herein blood refers to the plasma component, unless otherwise expressly stated or indicated in context), cerumen (ear wax), Cowper's fluid, chime, interstitial fluid, lymph fluids, mammalian milk, mucus, pleural fluid, pus, saliva, sebum, semen, serum, sweat tears, urine, vaginal secretion, vomit and exudates (from wounds or lesions).

The terms "subject" or "individual" or "patient" refer to any mammal, for example a human or a non-human primate, a domesticated mammal (e.g., canine or feline), an agricultural mammal (e.g., bovine, ovine, porcine, equine) or a laboratory mammal (e.g., rat, mouse, rabbit, hamster, guinea pig).

The terms "selective binding molecule," "antigen binding molecule" and "binding partner" interchangeably denote a molecule that selectively, but not necessarily specifically, binds to a particular target moiety. The binding is not random. Selective binding molecules may be selected from among various antibodies and antibody fragments or permutations thereof (e.g., poly- or monoclonal, peptibodies, humanized, foreshortened, mimetics, and others available in the art), aptamers (which may be DNA, RNA, or various protein forms, and may be further modified with additional functional moieties, such as enzymatic or colorimetric moieties), or may be particular to a particular biological system. Proteins may be expressed with particular "tags" such as a "His-tag", and a skilled practitioner will determine appropriate kinds of selective binding molecules or detectable labels are suitable. The list is not exhaustive.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

BRIEF DESCRIPTION OF THE DRAWINGS

FIG. 2 illustrates the use of the thermolabile microspheres as control reagents to track isolation cells of a rare cell population (e.g., CTCs) and analysis of genomic DNA of the isolated cells of the rare cell population. A. Labelled microspheres (e.g., with a fluorophore), having an average or mean diameter in the range of about 10-30 µm in size (e.g., about 20 µm), and attached to a hapten or immunogenic antigen, can be captured with cells of a rare population, e.g., retained in a microfluidic chip. B. Genomic DNA is isolated from the captured cells of the rare cell population and thermolabile microspheres. The cells and microspheres are exposed to heat as part of the process for isolating genomic DNA from the cells, causing heat-induced degradation or melting of the microspheres, releasing target polynucleotide contained within the microspheres. C. Genomic DNA and target polynucleotide are amplified and analyzed, e.g., based on amplification signal and/or sequencing.

DETAILED DESCRIPTION

1. Introduction

The embodiments disclosed herein are based, in part, on the development of synthetic stimulus-sensitive microparticles, e.g., microspheres, and their use to track one or more steps of a rare cell isolation process, including, e.g., cell labeling, recovery, DNA recovery, amplification of template, and/or detection limits of rare alleles. In various embodiments, the stimulus-sensitive microparticles (e.g., thermolabile microspheres) are used to control and index the recovery of the cells and to index the DNA sample during further manipulation and analysis. Analysis could be a variety of molecular assays such as, but not limited to, quantitative PCT (Q-PCR) and DNA sequencing. One consideration in isolating rare cells from whole blood is the actual efficiency of recovery for each particular isolation instance. In order to determine efficiency of rare cell recovery, we have developed a method of internal control. This internal control can be used to calibrate the performance of the isolation of cells from the biological sample and the isolation of genomic DNA from the isolated cells. The stimulus-sensitive microparticles (e.g., thermolabile fluorescent microspheres) can be used in a method for internal control and indexing. Our methodology supports clinical sample analysis. The reagent used for this application does not contain components that would confound subsequent molecular analysis.

2. Stimulus-Sensitive Microparticles a. Generally

Figure 1:
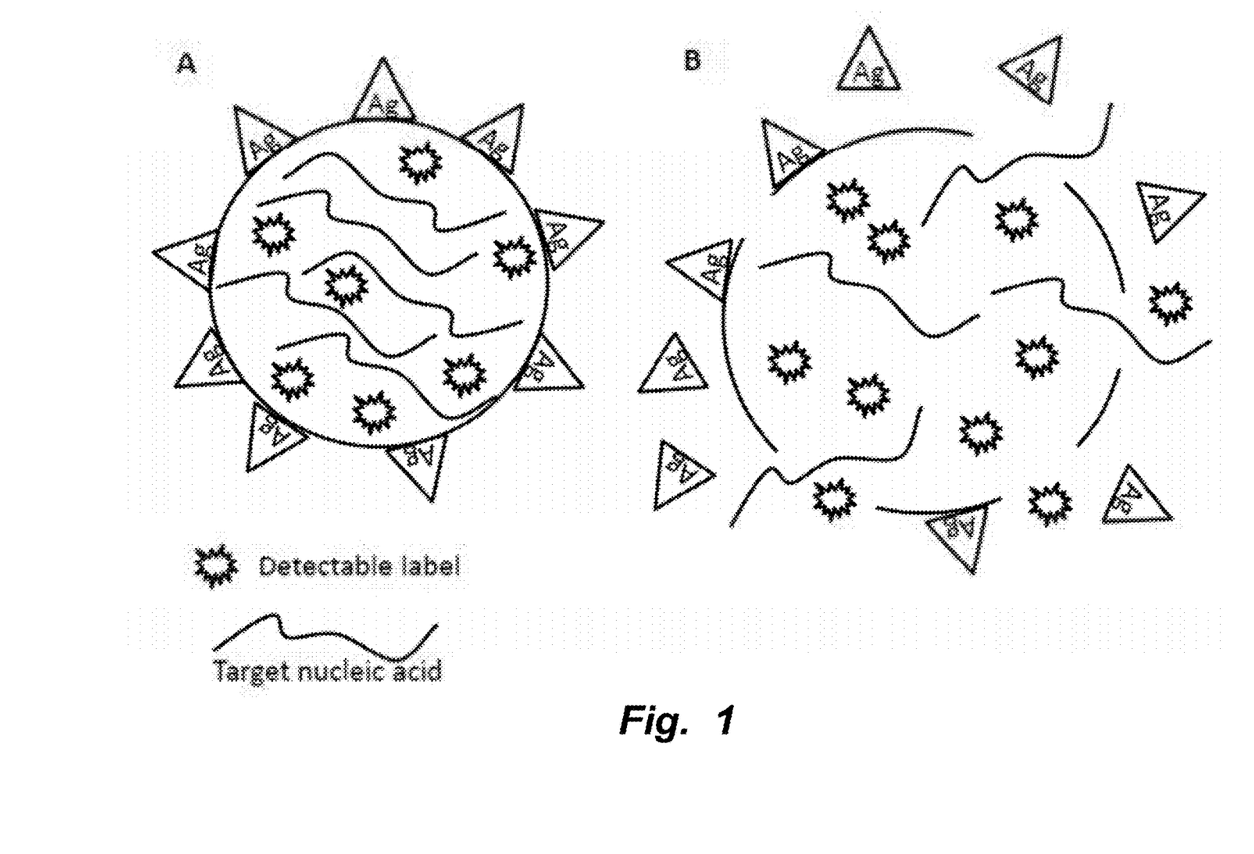
FIG. 1 illustrates a schematic of a stimulus-sensitive microparticle (e.g., thermolabile microsphere) attached to antigen (Ag) on its external surface and containing or encapsulating one or more reporting molecules (e.g., target polynucleotide and/or detectable label). The stimulus-sensitive microparticles (e.g., thermolabile microspheres) are intact when added to a biological sample (A) and melt or degrade upon exposure to a stimulus (e.g., a threshold temperatures, a threshold pH) for a time period sufficient to release the one or more reporting molecules (e.g., target polynucleotide and/or detectable label) (B).

Generally, the stimulus-sensitive microparticles (e.g., thermolabile microspheres) comprise a shell that dissolves and/or dissembles upon exposure to a stimulus (e.g., heat, pH, irradiation, light, an enzyme) and the shell is decorated on its external surface with an immunogenic epitope or antigen, or surface or other marker that can also be used to isolate the cells of the rare cell population (e.g., CTCs). One or more reporting molecules, e.g., a target polynucleotide sequence not found in the cells of the rare cell population, and optionally, a detectable label, can be encapsulated within the shell of the stimulus-sensitive microparticles.

Size/Shape:

In general, it is desired that the microparticle be of similar dimensions as the cell target. In various embodiments, the shape of the microparticle is a sphere, but the microparticles can be any appropriate shape mimicking the shape of the cells in the cell population being tracked, e.g., spherical, ellipsoid, rod-shaped. Prokaryotic cells are typically 1 to 5 µm in size, while Eukaryotic cells are 10-100 µm in size, thus the microparticle may satisfy a size ranging from 1 µm to 100 µm depending upon the specific application. The microparticles or microspheres can have an average diameter of the cells of the rare cell population being tracked, e.g., in the range of about 1-100 µm, e.g., about 20-30 µm, about 1-10 µm or about 10-100 µm, depending on whether prokaryotic or eukaryotic cells are being tracked.

Surface Properties:

The surface of the microparticle allows it to be purified or recognized by the methods described herein, e.g., antigen capture by antibody. In varying embodiments, the microparticles exhibit on their surface antigens that allow for antibody capture or to be otherwise distinguishable from sample cells. Decoration with an antigen or immunogenic epitope also allows for the microparticles to serve as a useful control during the FACS sorting of mixed cell populations. In varying embodiments, the surface capture antigen or immunogenic epitope can be a hapten such as digoxigen, other chemical or ligand such as biotin, or a protein recombinant or purified such as Epcam or IgG-Epcam fusion proteins, or a fluorophore that can be detected and enumerated.

Delivery & Detectability:

The microparticles may be detected by either or both visual and molecular methods. To permit both, the control can contain one or more reporting molecules that can be detected visually and/or by molecular methods. Thus any visual or molecular reporting molecules packaged into the microparticle can be used. This can include size and shape, surface epitopes that can be stained for separate evaluation, or encapsulation of dyes that allow direct colorimetric for fluorescent detection of the particles and/or polynucleotides or polypeptides which can be detected by molecular methods.

Composition:

The material composition of microparticles is designed to encapsulate or contain in its interior one or more reporting molecules. The material is also suitable for or capable of being surface labeled with a capture antigen or an immunogenic epitope. The microparticle, upon a change in physical state or upon exposure to a stimulus (e.g., a threshold temperature, a threshold pH, irradiation, light, contact with an enzyme), releases the one or more reporting molecules (e.g., target polynucleotide, detectable label). The chemical composition of the microparticle shell can be any of a number of suitable possibilities.

In various embodiments, the stimulus-sensitive shells of the microparticle can be composed of one or more polymers, a unilamellar micelle, a bilamellar micelle, a liposome, a dendrimer or dendrosome and/or carbon nanotubes. In various embodiments, the stimulus-sensitive microparticles degrade in aqueous buffers at elevated temperatures (3 hours at 55° C./1 hour 70° C.), e.g., are thermolabile. The microparticles can be derivatized, e.g., with a COOH or other chemical functionality, on their outer surface to enable attachment to one or more immunogenic epitopes or surface or other markers, e.g., biotin, Ep-CAM, or Digoxigenin, for concurrent isolation with the cells of the rare cell population, e.g., using magnetic separation techniques. The microparticles further contain one or more reporting molecules. For example, the stimulus-sensitive microparticles can be loaded with a detectable label, e.g., a fluorescent label, to facilitate visualization. The stimulus-sensitive microparticles can further contain a DNA target polynucleotide sequence. This DNA target can be a nucleic acid sequence that is not found in and does not amplify from the cells of the rare cell population (e.g., is non-human, mutated or synthetic) and can be concurrently quantified and analyzed (e.g., amplified and/or sequenced) with the genomic DNA isolated from the cells of the rare cell population.

In various embodiments, the stimulus-sensitive microparticles are introduced into whole blood prior to using antibodies or fragments thereof for the concurrent isolation of the rare cells and decorated stimulus-sensitive microparticles from the mixture of cells. Whole blood containing stimulus-sensitive microparticles can be antibody-labeled and fractionated using a solid substrate, e.g., magnets, beads, a microfluidic chip, to isolate all antibody labeled cells and microparticles. Cells and stimulus-sensitive microparticles can be quantified, e.g., by using fluorescent label to validate identity. Microparticle recovery is a measure of efficiency of recovery for chip performance.

In various embodiments, the cells of the rare cell population and stimulus-sensitive microparticles are recovered from a solid substrate and processed using DNA isolation procedures known in the art. DNA isolation procedures often involve elevated temperatures, e.g., to at least about 50° C. Thermolabile microparticles or microspheres sensitive to elevated temperatures (e.g., above about 50° C.) can be conveniently used for tracking efficiency of recovery of genomic DNA from the isolated cells of the rare cell population, such that the one or more reporting molecules (e.g., target polynucleotide and/or detectable label) are released from the microparticles as they degrade upon exposure to the threshold temperature. The target polynucleotides are subsequently quantified and/or analyzed along with the genomic DNA isolated from the cells of the rare cell population using methods known in the art.

In various embodiments, the stimulus-sensitive microparticles are not recovered by magnetic capture but used as controls for isolation of rare events. In such embodiments, the stimulus-sensitive microparticles can be labeled with a detectable label that can be sorted. In some embodiments, the stimulus-sensitive microparticles are labeled with a fluorophore, mixed with a mixture of cells comprising cells of a rare cell population, and the mixture of cells is sorted by fluorescent activated cell sorting (FACS). Labeled stimulus-sensitive microparticles identified by sorting are representative of the cells of rare cell population in the mixture of cells subject to sorting. In such embodiments, magnetic capture may not be performed but fluorescent sorting and molecular analysis may still be conducted. The stimulus-sensitive microparticles and cells of the rare cell population may be captured by the cell sorting process, as desired.

b. Microparticle Shells i. Temperature Sensitive Shells

In varying embodiments, the microparticle is thermolabile or thermoresponsive, and degrades upon exposure to a threshold temperature.

For example, in some embodiments, the shell of the thermolabile microparticle or microsphere is comprised of one or more polymers. In varying embodiments, the one or more polymers used in the thermolabile microparticles or microspheres have a sharp melting point, e.g., undergoes a transition from solid phase to a melt phase/flow phase/liquid phase over 10 or fewer ° C., e.g, over 9, 8, 7, 6, 5 or fewer ° C. In varying embodiments, the polymer is a homopolymer. In varying embodiments, the polymer is comprised of monomers of substantially uniform molecular weight (e.g., monomers having a variance of molecular weight of about 10% or less, where molecular weight is determined according to the number average molar mass statistical method).

In certain embodiments, the one or more polymers melt or undergo degradation in an aqueous solution sufficient to release target polynucleotide at a temperature corresponding to the temperature of a process step used to release nucleic acid from the rare cells. In various embodiments, the one or more polymers melt (i.e., undergo the transition from solid phase to a melt phase/flow phase/liquid phase) or degrade in an aqueous solution at a temperature above about 50° C., for example, at a temperature above about 55° C., 60° C., 65° C. or 70° C., over a period of time sufficient to release target polynucleotide contained in the microparticle or microsphere. For example, in various embodiments, the melting or degradation of the microparticle or microsphere occurs upon exposure to elevated temperatures over a period of 5 or fewer hours, e.g., 5, 4, 3, 2, 1 or 0.5 hours (e.g., 3 hours at 55° C. or 1 hour 70° C.). Degradation or melting occurs over a shorter period of time the higher the temperature. Preferably, the one or more thermolabile polymers in the solid phase are impermeable to the one or more reporting molecules (e.g., target polynucleotide and/or detectable label) contained within the microparticle. Thermolabile polymers are known in the art and can find use in the present microparticles.

In various embodiments, the polymer used is biodegradable and/or biocompatible. In some embodiments, the thermolabile polymer is selected from the group consisting of polycaprolactone (PCL), poly L-lysine (PLL), polystyrene, polymethyl methacrylate (PMMA), Poly Lactic-co-Glycolic Acid (PLGA), polyisopropyl acrylamide, butyl vinyl ether, cis-chlorobutadiene, ethylene adipate, ethylene oxide, ethylene vinyl acetate, ethyl vinyl ether, trans-isoprene, poly (hexene 1), poly(methyl methacrylate), poly(vinyl chloride), propylene oxide, propyl vinyl ether and vinyl acetal. In some embodiments, the thermolabile polymer is a biodegradable polyester. In some embodiments, the thermolabile polymer is selected from the group consisting of polycaprolactone (PCL), poly L-lysine (PLL), polystyrene, polymethyl methacrylate (PMMA), and Poly Lactic-co-Glycolic Acid (PLGA). In some embodiments, the thermolabile polymer is polycaprolactone (PCL). In some embodiments, the polycaprolactone (PCL) comprises a molecular weight in the range of about Mn 10,000 to about Mn 90,000, e.g., about Mn 10,000-14,000, Mn 45,000, or Mn 70,000-90,000, where Mn refers to number average molar mass. In some embodiments, the thermolabile polymer is a polyhydroxyalkanoate.

Other materials also find use in the preparation of thermolabile microparticle shells, including those described in Curcio, et al., *AAPS Pharm Sci Tech*. (2010) 11(2):652-62; Cirillo, et al., *J Biomater Sci Polym Ed*. (2011) 22(4-6):823-44; Curcio, et al., *Eur J Pharm Biopharm*. (2010) 76(1):48-55; Huang, et al., *Electrophoresis*. (2011) 32(23):3364-70; Joshi, et al., *Acta Biomater*. (2013) 9(5):6526-34; and Ma, et al., *J Biomed Mater Res B Appl Biomater*. 2011 Nov. 25. doi: 10.1002/jbm.b.31900. Curcio, et al., *AAPS Pharm Sci Tech*. (2010) describe hydrogels synthesized by free-radical polymerization of hydrolyzed methacrylated gelatin (HGel-MA) and N,N'-methylenebisacrylamide as pro-hydrophilic multifunctional macromer and crosslinker, respectively, and N-isopropylacrylamide as thermo-responsive monomer, and which have a transition temperature of about 36-37° C. Cirillo, et al., describe dual thermo- and pH-sensitive microparticles comprised of methacrylate bovine serum albumin (BSA-MA) as cross-linker and sodium methacrylate (NaMA) and/or N-isopropylacrylamide (NIPAAm). Curcio, et al., *Eur J Pharm Biopharm*. (2010) describe microspheric hydrogels synthesized by grafting of N-isopropyacrylamide (NIPAAm) with gelatin, which have a transition temperature in the range of about 34-35° C. Huang, et al., describe tunable microparticles comprising poly(N-isopropylacrylamide) (PNIPAM) and tuned by addition of polyethylene glycols (PEGs) of varying sizes and at varying ratios. Joshi, et al., describe dual thermo- and pH-sensitive microparticles comprised of N-isopropyl acrylamide (NIPAAm), propyl acrylic acid (PAA), and butyl acrylate (BA). Ma, et al., describe pH- and temperature-sensitive self-assembly microcapsules/microparticles comprising carboxymethyl chitosan (CMCTS) and carboxymethyl chitosan-graft-poly(N,N-diethylacrylamide) (CMCTS-g-PDEA).

In varying embodiments, the polymer has functional groups on the external surface of the microparticle for the chemical attachment or derivitization of one or more immunogenic epitopes or surface or other markers. Functional groups for derivatization are known in the art and can be used. Illustrative functional groups include, carboxyl, amino, amido, carbonyl, imido, carbodiimide, hydroxysuccinimide, sulhydryl, azide, diazirine, maleimide, isocyanate, thiol, hydrazide, aldehyde and anhydride. Reagents for crosslinking, derivatizing and modifying are commercially available, e.g., from ThermoFisher Scientific (piercenet. com).

ii. pH-Responsive Shells

In varying embodiments, the microparticle shell is responsive to or dissolves upon exposure of the shell to a threshold pH. pH-responsive microparticle shell compositions are known in the art and can find use in the present microparticles. For example, Kondiah, et al., *Int J Pharm*. 2013 Sep. 1. pii: S0378-5173(13)00771-0 describe pH-sensitive microparticles prepared using trimethyl-chitosan (TMC), poly(ethylene glycol)dimethacrylate (PEGDMA) and methacrylic acid (MAA). Lee, et al., *Drug Deliv*. (2010) 17(8):573-80 describe pH-responsive poly(methacrylic acid (MAA)-co-ethylene glycol methacrylate (EGMA)) hydrogel microparticles. Zhang, et al., *Langmuir*. (2013) 29(1):65-74 describe pH-sensitive microparticles comprised of oleamide derivatives.

iii. Liposomal and Micellar Shells

In varying embodiments, the microparticle shell is comprised of a liposome, or unilamellar or bilamellar micelles. Thermosensitive and pH-sensitive liposomal compositions are known in the art and can find use in the present microparticles, including without limitation those described in, e.g., Caldeira de Araújo Lopes, et al., *Biomed Res Int*. (2013) 2013:467147; Ferreira Ddos, et al., *Ther Deliv*. (2013) 4(9):1099-123; Hossann, et al., *J Control Release*. (2010) 147(3):436-43; Kheirolomoom, et al., *J Control Release*. 2013 Aug. 28. pii: S0168-3659(13)00478-1; Kim, et al., *ACS Appl Mater Interfaces*. (2013) 5(12):5648-58; Laouini, et al., *ACS Appl Mater Interfaces*. 2013 Sep. 3 (PMID: 23947913); Li, et al., *Int J Biol Macromol*. 2013 Aug. 31. pii: S0141-8130(13)00465-0; Li, et al., *Int J Biol Macromol*. (2013) 55:69-74; Li, et al., *J Biomed Mater Res A*. 2013 Jul. 27. doi: 10.1002/jbm.a.34894; Needham, et al., *Faraday Discuss*. (2013) 161:515-34; Won, et al., *J Nanosci Nanotechnol*. (2013) 13(6):3792-800; and Zhang, et al., *Int J Biol Macromol*. (2012) 51(5):1109-15.

iv. Dendrimers and/or Dendrosomes

In varying embodiments, the microparticle shell is comprised of dendrimers or dendrosomes. Thermosensitive and pH-sensitive dendrimers and dendrosomes are known in the art and can find use in the present microparticles, including without limitation those described in, e.g., Bikram, et al., *Expert Opin Drug Deliv*. (2008) 5(10):1077-91; Chen, et al., *Chemistry*. (2013) 19(33):11051-61; Kojima, et al., *Biopolymers*. 2013 Jul. 26. doi: 10.1002/bip.22276; Li, et al., *Bioconjug Chem*. (2013) 24(2):282-90; Rajasekhar, et al., *New J Chem*. (2012) 36(2):340-349; Zhao, et al., *Int J Pharm*. (2011) 409(1-2):229-36; and Adeli, et al., *Nanomedicine*. 2013 Jun. 6. pii: S1549-9634(13)00264-5.

c. Reporting Molecules

The stimuli-sensitive microparticles generally comprise within the interior space of the shell one or more reporting molecules. In varying embodiments, the one or more reporting molecules comprise a target polynucleotide and/or a detectable label.

i. Target polynucleotide

In some embodiments, the microparticles contain or encapsulate within their interior space a target polynucleotide. In various embodiments, the target polynucleotide is a polynucleotide sequence that is not found in and cannot be amplified or sequenced from the cells of the rare cell population (e.g., CTCs). In some embodiments, the target polynucleotide is a sequence variant with distinguishable amplification performance from the analogous sequence in the cells of the rare cell population (e.g., CTCs). In various embodiments, the target polynucleotide is a polynucleotide sequence that is not mammalian or that is non-human. In various embodiments, the target polynucleotide is a polynucleotide sequence that is a mutated human DNA sequence or a synthetic or artificial DNA sequence. The target polynucleotide is generally of a size that can be completely contained within a microparticle. In varying embodiments, the target polynucleotide is part of or within a plasmid. In various embodiments, the target polynucleotide can be DNA and/or RNA, or derivatives or analogs thereof.

One example target polynucleotide comprises a polynucleotide encoding plasmid maintenance protein (ccdB). Another example target polynucleotide comprises a polynucleotide encoding 3',5'-cyclic adenosine monophosphate phosphodiesterase cpdA.

ii. Detectable Label

In some embodiments, the microparticles are attached to or contain or encapsulate within their interior space a detectable label. Generally, the detectable label used can be detected using any means known in the art while it is contained within the microparticle. In varying embodiments, the detectable label is a fluorophore, a photoluminescent label or a radioactive label.

In some embodiments, the detectable label is a fluorophore. Illustrative fluorophores include without limitation a xanthene derivative (e.g., fluorescein, rhodamine, Oregon green, eosin, and Texas red) a cyanine derivative (e.g., cyanine, indocarbocyanine, oxacarbocyanine, thiacarbocyanine, and merocyanine), a naphthalene derivative (e.g., dansyl and prodan derivatives), a coumarin derivative (e.g., hydroxycoumarin, methoxycoumarin and aminocoumarin), an oxadiazole derivative (e.g., pyridyloxazole, nitrobenzoxadiazole and benzoxadiazole), a pyrene derivative (e.g., cascade blue), an oxazine derivative (e.g., Nile red, Nile blue, cresyl violet, oxazine 170), an acridine derivative (e.g., proflavin, acridine orange, acridine yellow), an arylmethine derivative (e.g., auramine, crystal violet, malachite green), and a tetrapyrrole derivative (e.g., porphin, phtalocyanine, bilirubin). In some embodiments, the fluorophore is a fluorescein, e.g., FAM or fluorescein isothiocyanate.

In varying embodiments, the detectable label is a radioactive isotope. Radiolabels that find use include without limitation $^{3}H$, $^{125}I$, $^{35}S$, $^{14}C$, $^{32}P$, $^{99}Tc$, $^{203}Pb$, $^{67}Ga$, $^{68}Ga$, $^{72}As$, $^{111}In$, $^{113}In$, $^{97}Ru$, $^{62}Cu$, $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{177}Lu$, $^{105}Rh$, and $^{111}Ag$.

In various embodiments, the detectable label can be a photoluminescent component. The photoluminescent component can be any known or available probe, metal, or semiconductor material which can be detected by photodetection. An illustrative photoluminescent component is a nanocrystal of semiconducting materials, including without limitation "quantum dots" (QDs), quantum rods (QRs), and quantum wires (QWs). QDs, QRs, and QWs have several advantages over conventional fluorescent dyes, including a long luminescent lifetime and near quantitative light emission at a variety of preselected wavelengths. QDs typically contain a semiconductor core of a metal sulfide or a metal selenide, such as zinc sulfide (ZnS), lead sulfide (PbS), or, most often, cadmium selenide (CdSe). Non-heavy metal-based QDs have also been reported. QDs typically have diameters of 1 to about 20 nm, depending on the emission wavelength desired, thickness of coating. In one embodiment, the inorganic core comprises a fluorescent semiconductor nanocrystal or metal nanoparticle. Quantum dot labels that find particular use are those that are biocompatible. Such quantum dots usually have layers of organic coating to make them hydrophilic, biocompatible, and present specific chemical groups. Biocompatible fluorescent nanocrystals refer to core/shell structure quantum dots including CdSe/ZnS, generally having a hydrophilic polymer coating, silica, derivatized surface with biomolecules such as streptavidin, nucleotides, peptides, or chemical groups. See, e.g., Gerion, et al., *Journal of Physical Chemistry* (2001) 105(37):8861-8871; Pathak, et al., *J. Am. Chem. Soc.* (2001) 123(17):4103-4104; Chan, et al., *Current Opinion in Biotechnology* (2002) 13(1):40-46; Larson, et al., *Science* (2003) 300(5624):1434-1436; Jaiswal, et al., *Nature Methods* (2004) 1(1):73-78; Jaiswal, et al., *Trends in Cell Biology* (2004) 14(9):497-504; Alivisatos, et al., *Annual Review of Biomedical Engineering* (2005) 7:55-76; Bentzen, et al., *Bioconjugate Chemistry* (2005) 16(6):1488-1494; Parak, et al., *Nanotechnology* (2005) 16:R9-R25; Selvan, et al., *Advanced Materials* (2005) 17(13):1620-1625; Jiang, et al., *Chemistry of Materials* (2006) 18(20):4845-4854. Moreover, Michalet, et al., *Science* (2005) 307(5709):538-544; and Klostranec, et al., *Advanced Materials* (2006) 18(15): 1953-1964 provide extensive reviews on surface polymer coatings for quantum dots. Quantum dots of use are commercially available, e.g., from Ocean NanoTech (oceannanotech.com), NN-Labs (nn-labs.com), Cytodiagnostics (cytodiagnostics.com) and Life Technologies (lifetechnologies.com).

d. Immunogenic Epitope or Antigen Attached to External Surface

In some embodiments, the microparticles are decorated with or have attached on the external surface of the polymer to one or more immunogenic epitopes or surface or other markers. Generally, the one or more immunogenic epitopes or surface or other markers are the same epitopes or markers used to isolate the cells of the rare cell population (e.g., CTCs) from the mixture of cells. Note that the "same" epitope or surface marker on the surface of the microparticle need not in all implementations be chemically identical to the epitope or marker used to isolate the rare cell population. However, such epitope or surface marker on the microparticles should mimic the epitope or marker on the rare cells insofar as binding with the binding partner is concerned. Typically, epitopes or markers on the microparticles and rare cells will be either chemically identical or have closely similar affinities and selectivities for the binding partner.

In various embodiments, the immunogenic epitope or surface or other marker is expressed on the surface of the cells of the rare cell population. In embodiments where the rare cell population is circulating tumor cells (CTC), the one or more epitopes attached to the external surface of the polymer are from CTC-associated marker. Illustrative CTC-associated markers include, e.g., Epithelial cell adhesion molecule (Ep-CAM), keratin 19 (KRT19), mucin 1 (MUC1), carcinoembryonic antigen-related cell adhesion molecule 5 (CEACAM5), baculoviral IAP repeat containing 5 (BIRC5), secretoglobin, family 2A, member 2 (SCGB2A2), and ERBB2. In some embodiments, the immunogenic epitope or surface or other marker is selected from biotin, Ep-CAM or digoxigenin.

In other examples, illustrative markers for fetal erythrocytes include fetal erythrocyte antigen and CD71. Illustrative positive markers of human bone marrow-derived mesenchymal stem cells include, e.g., CD10, CD13, CD15, CD29, CD44, CD49d, CD49e, CD51, CD54, CD56, CD71, CD73, CD90, CD105, CD106, CD117, CD120a, CD120b, CD166, CD271 and CD309. Illustrative human pluripotent stem cell markers include, e.g., TRA-1-81 and SSEA-3. Illustrative cancer stem cell markers include, e.g., CD13, CD133, CD34, CD44, cytokeratins (CK5, CK14, CK17), AFP/alpha-fetoprotein; L1CAM/CD107; beta-Catenin/CTNNB1; LMO2; BMI-1; CD64/Fe gamma RI; Nodal; BMP-4; CD74; Notch-1; CD2; CD90/THY-1; PDGFRB/CD140b; CD3d; CD96; Podoplanin; CD3e; CD123/IL3RA; PTEN; CD3g; CD166/ALCAM; Sonic Hedgehog; CD16/Fr gamma RIII; c-Kit/CD117; STAT3; CD18; CXCL12/SDF-1; Syndecan-1/SDC1/CD138; CD19; CXCR4; Transferrin Receptor/TFRC/CD71; CD20/MS4A1; Decorin; Vimentin; CD27; E-Cadherin/Cadherin 1; CD29/Integrin beta 1/ITGB1; EGFR/ErbB1; CD31/PECAM-1; Endoglin/CD105; CD34; EpCAM/TROP-1; CD38; Fe epsilon RI A/FCER1A, and those summarized in Klonish, et al., *Trends in Molecular Medicine*, (2008) 14(10)450-460. Additional cancer stem cell markers include, e.g., Bladder Cancer Stem Cell Markers (e.g., CD44 and CD47); Breast Cancer Stem Cell Markers (e.g., Aldehyde Dehydrogenase 1-A1/ALDH1A; GLI-1; BMI-1; GLI-2; CD2; IL-1 alpha/IL-1F1; CD4; IL-6R alpha; CXCR4; CXCR1/IL-8 RA; DLL4 Integrin alpha 6/CD49f; EpCAM/TROP; PTEN; ErbB2/Her2); Colon Cancer Stem Cell Markers (e.g., ALCAM/CD166; EpCAM/TROP1; Aldehyde Dehydrogenase 1-A1/ALDH1A1; GLI-1; CD44; Musashi-1; DPPIV/CD26); Gastric Cancer Stem Cell Markers (e.g., CD44 and DLL4); Glioma/Medulloblastoma Cancer Stem Cell Markers (e.g., A20/TNFAIP3; Integrin alpha 6/CD49f; ABCG2; L1CAM; CX3CL1/Fractalkine; Musashi-1; CX3CR1 c-Mye; CXCR4; Nestin; HIF-2 alpha/EPAS1; Podoplanin; IL-6 R alpha); Head & Neck Cancer Stem Cell Markers (e.g., ABCG2; BMI-1; Aldehyde Dehydrogenase 1-A1/ALDH1A1; CD44) Leukemia Cancer Stem Cell Markers (e.g., BMI-1 GLI-2; CD34; IL-3 R alpha; CD38 MICL/CLEC12A; CD44; Musashi-2; CD47; SCF R/c-kit; CD96; TIM-3; GLI-1); Liver Cancer Stem Cell Markers (e.g., alpha-Fetoprotein/AFP CD90/Thy1; Aminopeptidase N/ANPEP; NF2/Merlin); Lung Cancer Stem Cell Markers (e.g., ABCG2; EpCAM/TROP1; Aldehyde Dehydrogenase 1-A1/ALDH1A1; SCF R/c-kit; CD90/Thy1); Melanoma Cancer Stem Cell Markers (e.g., ABCB5; MS4A1/CD20; ABCG2 Nestin; ALCAM/CD166; NGF; R/TNFRSF16); Myeloma Cancer Stem Cell Markers (e.g., CD19; MS4A1/CD20;CD27/TNFRSF7; Syndecan-1/CD138; CD38); Osteosarcoma Cancer Stem Cell Markers (e.g., ABCG2; STRO-1; Nestin); Ovarian Cancer Stem Cell Markers (e.g., alpha-Methylacyl-CoA Racemase/AMACR; SCF R/c-kit; CD44); Pancreatic Cancer Stem Cell Markers (e.g., BMI-1; CXCR4;CD24; EpCAM/TROP1; CD44); Prostate Cancer Stem Cell Markers (e.g., ABCG2; CD44; alpha-Methylacyl-CoA Racemase/AMACR e-Mye; BMI-1).

Figure 2:
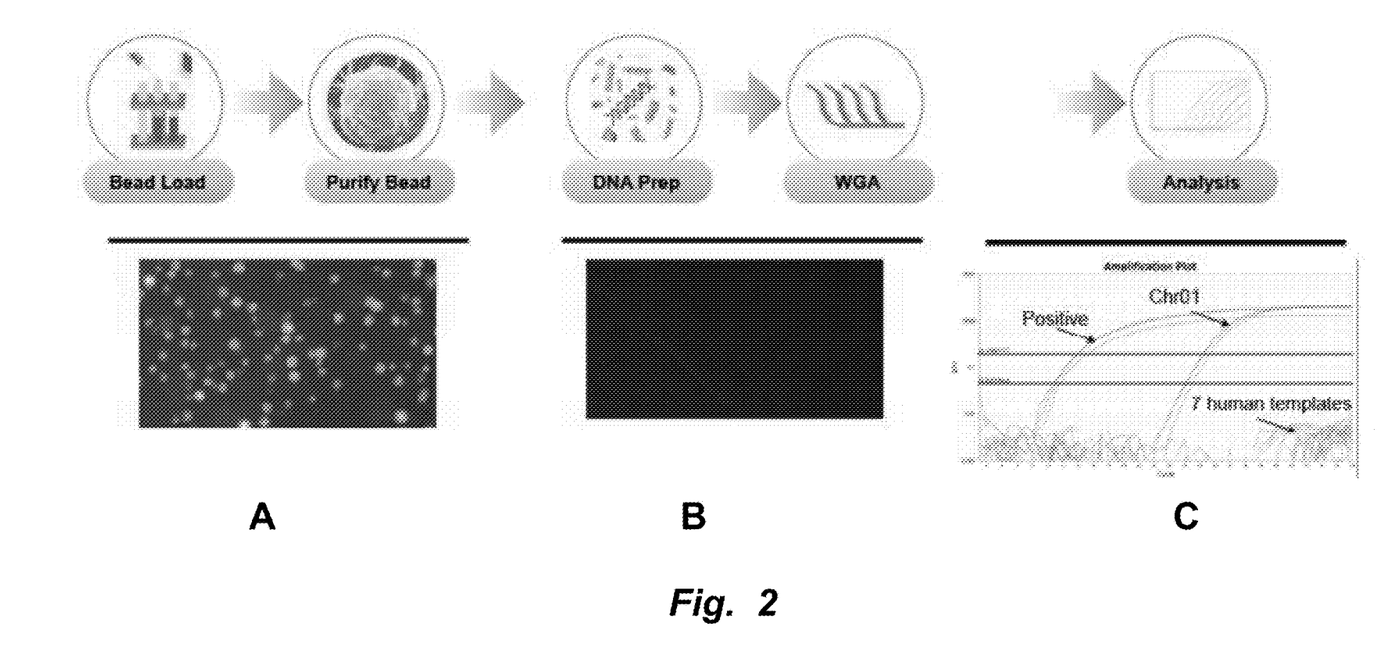

3. Methods of Tracking Recovery of a Rare Cell Population from a Mixture of Cells a. Generally The microparticles find use in monitoring the capture and recovery of cells in a rare cell population from a complex mixture. The microparticles serve as an internal process control and can be designed or selected to be of an approximate shape and size of the cells of interest to be tracked and can be used to monitor the efficiency and accuracy of capture, recovery and processing of a sample throughout the entire process (e.g., starting with capture from a complex mixture and concluding with genomic DNA analysis). In various embodiments, the microparticles, as described above and herein, are spiked or introduced into a mixture of cells (e.g., a whole blood) prior to exposure to the binding partner. The mixture of cells containing the stimulus-sensitive microparticles (e.g., thermolabile microspheres) is then contacted with a binding partner to the immunogenic epitope or surface or other marker for isolating the microparticles and the cells of the rare cell population (e.g., CTCs). The binding partner can be attached to a solid substrate (e.g., a bead, a magnet, a microfluidic chip) that allows for the selective and concurrent isolation of the cells of the rare cell population and microparticles from the mixture of cells. Isolated cells and microparticles are counted by using a detectable label attached to the binding partner and/or the stimulus-sensitive microparticles (e.g., thermolabile microspheres). Microparticle recovery is a measure of efficiency of recovery of the cells of the rare cell population from the mixture of cells. In certain embodiments, the bound cells and microparticles are isolated using a magentophoretic technique. In some implementations, magnetophoretic isolation is accomplished using a microfluidic chip in which a sample stream and one or more buffer streams are concurrently introduced to an isolation chamber in laminar streams. An example of such technique employing sheath flow chips is described in U.S. patent application Ser. No. 12/813,285 filed Jun. 10, 2009, published as 2011/0003303, which is incorporated herein by reference in its entirety.

In varying embodiments, cells of the rare cell population and microparticles are recovered from the solid substrate and subject to genomic DNA isolation procedures known in the art. Genomic DNA isolation procedures generally involve elevated temperatures (e.g., above about 50° C.) and are compatible with use of thermolabile microparticles. Exposure of the thermolabile microparticles to threshold temperatures liberates or releases the one or more reporting molecules (e.g., target polynucleotide sequence) from the microparticles as they dissolve and/or degrade. The target polynucleotide released from the microparticles and the genomic DNA from the cells of the rare cell population are concurrently quantified and analyzed (e.g., amplified and/or sequenced) using methods known in the art.

b. Mixing a Predetermined Number of Stimuli-Sensitive Microparticles with a Mixture of Cells Suspected of Comprising a Cell of a Rare Cell Population A predetermined number of the stimulus-sensitive microparticles (e.g., thermolabile microspheres) is added to and homogenously mixed into (e.g., evenly distributed throughout) a biological sample comprising a mixture of cells suspected of comprising one or more cells of a rare cell population (e.g., CTCs).

In various embodiments, the methods further comprise the step of obtaining a biological sample suspected of comprising one or more cells of the rare cell population. The biological sample can comprise cultured cells or can be obtained from a subject. In various embodiments, the biological sample from the subject is a fluid biological sample, e.g., amniotic fluid, aqueous humor, blood and blood plasma (and herein blood refers to the plasma component, unless otherwise expressly stated or indicated in context), cerumen (ear wax), Cowper's fluid, chime, interstitial fluid, lymph fluids, mammalian milk, mucus, pleural fluid, pus, saliva, sebum, semen, serum, sweat tears, urine, vaginal secretion, vomit and exudates (from wounds or lesions).

In some embodiments, the biological sample is a whole blood sample from a subject. In cases where the rare cell population sought to be analyzed is CTC, the subject is suspected of having CTC in the biological sample, e.g., in a whole blood sample.

The predetermined number of the stimulus-sensitive microparticles (e.g., thermolabile microspheres) added may depend on the volume of the sample or the number of cells of the rare cell population suspected of being contained in the sample. The number of microparticles added to the sample comprising the mixture of cells is typically in the range of 10-100 microparticles, e.g., 10, 20, 25, 30, 40, 50, 60, 70, 75, 80, 90 or 100 microparticles. In some embodiments, the number of stimulus-sensitive microparticles (e.g., thermolabile microspheres) added to the biological sample is determined based on the level of resolution for recovery to be evaluated. For example, to validate the high resolution of recovery of a low number of cells of the rare cell population, a low number of microparticles (e.g., fewer than 20 microparticles, e.g., 10, 9, 8, 7, 6 or 5 microparticles) are added to the biological sample. In various embodiments, two different microparticles (e.g., microparticles having different target polynucleotide sequences or having different immunogenic epitopes or surface or other markers) can be spiked into blood samples at two different concentrations, low and high. For instance, for low concentration, about 10 spheres are mixed into the biological sample; for high concentration, about 100 spheres are mixed into the biological sample.

c. Adding Binding Partner that Binds to the Immunogenic Epitope or Surface or Other Marker on the Stimulus-Sensitive Microparticles and Cells of Rare Cell Population After the microparticles are spiked or mixed in with the mixture of cells in the biological sample suspected of comprising one or more cells of the rare cell population (e.g., CTCs), the biological sample comprising the microparticles and the cells is contacted with one or more binding partners or antigen binding molecules that bind to the immunogenic epitopes or surface or other markers attached to the external surface of the microparticles and on or within the cells of the rare cell population under conditions that allow for the binding of the binding partners or antigen binding molecules to the immunogenic epitopes or surface or other markers. The one or more binding partners or antigen binding molecules can be antibodies (or fragments thereof) or non-antibody molecules.

i. Antibodies or Fragments Thereof that Bind to the Epitope

In various embodiments, the binding partner or antigen binding molecule is an antibody or antibody fragment that binds to the immunogenic epitope. Antibodies that bind to the immunogenic epitope (e.g., CTC marker) for use in the present methods include without limitation, polyclonal antibodies, monoclonal antibodies, chimeric antibodies, humanized antibodies, human antibodies, and fragments thereof.

Antibody fragments for use in the present methods can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a fragment denoted F(ab')$_2$. This fragment can be further cleaved using a thiol reducing agent, and optionally a blocking group for the sulfhydryl groups resulting from cleavage of disulfide linkages, to produce Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also, Nisonhoff, et al., Arch. Biochem. Biophys. 89:230 (1960); Porter, Biochem. J. 73:119 (1959): Edelman et al., METHODS IN ENZYMOLOG Y, VOL. 1, page 422 (Academic Press 1967); and Coligan et al. *Current Protocols in Immunology*, Wiley, updated through Aug. 1, 2012, e.g., at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques can also be used, so long as the fragments bind to the antigen that is recognized by the intact antibody.

For example, Fv fragments comprise an association of VH and VL chains. This association can be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See. e.g., Sandhu, *Crit Rev Biotechnol.* 1992; 12(5-6):437-62. In some embodiments, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFv are described, for example, by Whitlow et al, METHODS: A COMPANION TO METHODS IN ENZYMOLOGY, VOL. 2, page 97 (1991); Bird et al, Science 242:423-426 (1988); Ladner, et al, U.S. Pat. No. 4,946,778; Pack, et al, BioTechnology 11:1271 77 (1993); and Sandhu, supra.

Another form of an antibody fragment suitable for use with the present methods is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al, METHODS: A COMPANION TO METHODS IN ENZYMOLOG Y, VOL. 2, page 106 (1991), iv. Small Organic Compounds.

In some embodiments, the anti-epitope antibody is a single-domain antibody (sdAb) or a nanobody. A single-domain antibody or a nanobody is a fully functional antibody that lacks light chains; they are heavy-chain antibodies containing a single variable domain (VHH) and two constant domains (CH2 and CH3). Like a whole antibody, single domain antibodies or nanobodies are able to bind selectively to a specific antigen. With a molecular weight of only 12—15 kDa, single-domain antibodies are much smaller than common antibodies (150—160 kDa) composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Antibodies that specifically bind to Ep-CAM are commercially available and can find use, e.g., from EMD Millipore (millipore.com), OriGene (origene.com), Abcam (abcam.com), Cell Signaling Technology (cellsignal.com), StemCell Technologies (stemcell.com), R&D Systems (rndsystems.com), eBioscience (ebioscience.com), Santa Cruz Biotechnology (scbt.com) and Miltenyi Biotec (miltenybiotec.com). Antibodies that specifically bind to digoxigenin are commercially available and can find use, e.g., from Origene, Acris Antibodies (us.acris-antibodies.com), Abcam, Life Technologies, Santa Cruz Biotechnology, Novus Biologicals (novusbio.com).

ii. Non-Antibody Binding Partners or Antigen Binding Molecules

In various embodiments, the binding partner or antigen binding molecule is a non-antibody binding protein. Protein molecules have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (Proc. Natl. Acad. Sci. U.S.A. 92(14):6552-6556 (1995)) discloses an alternative to antibodies based on cytochrome b562. Ku et al. (1995) generated a library in which two of the loops of cytochrome b562 were randomized and selected for binding against bovine serum albumin. The individual mutants were found to bind selectively with BSA similarly with anti-BSA antibodies.

Lipovsek el al. (U.S. Pat. Nos. 6,818,418 and 7,115,396) discloses an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. Any technique for evolving new or improved binding proteins can be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling can be employed in vitro that is similar to the process of affinity maturation of antibodies in vivo.

Beste et al. (Proc. Natl. Acad. Sci. U.S.A. 96(5): 1898-1903 (1999)) discloses an antibody mimic based on a lipocalin scaffold (Anticalin®). Lipocalins are composed of a β-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Anticalins® are small, single chain peptides, typically between 160 and 180 residues, which provide several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (Cell. Mol. Biol. 49(2):209-216 (2003)) discusses a methodology for reducing antibodies into smaller peptidomimetics, they term "antibody like binding peptidomimetics" (ABiP) which can also be useful as an alternative to antibodies.

Silverman el al. (Nat. Biotechnol. (2005), 23: 1556-1561) discloses fusion proteins that are single-chain polypeptides comprising multiple domains termed "avimers." Developed from human extracellular receptor domains by in vitro exon shuffling and phage display the avimers are a class of binding proteins somewhat similar to antibodies in their affinities and specificities for various target molecules. The resulting multidomain proteins can comprise multiple independent binding domains that can exhibit improved affinity (in some cases sub-nanomolar) and specificity compared with single-epitope binding proteins. Additional details concerning methods of construction and use of avimers are disclosed, for example, in U.S. Patent App. Pub. Nos. 2004/0175756, 2005/0048512, 2005/0053973, 2005/0089932 and 2005/0221384.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics) all of which are suitable for use with the present methods. Streptavidin and related molecules (e.g., avidin, streptavidin, NeutrAvidin and CaptAvidin) can be used to bind to biotin. Such avidin analogues and conjugates are commercially available, e.g., from Life Technologies.

d. Concurrently Isolating Binding Partner-Bound Microparticles and Cells of the Rare Cell Population from the Biological Sample The methods further comprise the step of concurrently isolating the cells of the rare cell population with the stimulus-sensitive microparticles (e.g., thermolabile microspheres) mixed into the biological sample. The cells of the rare cell population (e.g., CTCs) and microparticles can be isolated using any appropriate or applicable method known in the art. In some embodiments, the rare cell population can be isolated based on the surface expression of an immunogenic epitope or marker. For example, a solid support attached to a cognate binding partner of the immunogenic epitope or marker can be used to capture and isolate the cells of the rare cell population. In various embodiments, the solid support is a magnetic bead attached (e.g., conjugated or covalently bound) to a cognate binding partner of a marker. In some embodiments, the solid support is a chip, e.g., a microfluidic chip. Such methods are known in the art.

In embodiments where the rare cell population is a CTC, the CTC and microparticles can be concurrently concentrated and/or isolated based on their expression of one or more known CTC-associated markers, e.g., Epithelial cell adhesion molecule (Ep-CAM), keratin 19 (KRT19), mucin 1 (MUC1), carcinoembryonic antigen-related cell adhesion molecule 5 (CEACAM5), baculoviral IAP repeat containing 5 (BIRC5), secretoglobin, family 2A, member 2 (SCGB2A2), and ERBB2. Cognate binding partners to such surface expressed markers (e.g., a cognate ligand or antibody that binds to the marker) can be attached to a solid support, e.g., magnetic beads, and used to concentrate and/or isolate the CTC. In various embodiments, the CTC in a biological sample are enriched by removing CD45+ leukocytes from cells in the sample.

Methods for concentrating and/or isolating CTC described in the art find use for the concurrent isolation of CTC and stimulus-sensitive microparticles (e.g., thermolabile microspheres). Illustrative methods for concentrating and/or isolating CTC are taught, e.g., in U.S. Patent Publication Nos. 2011/0137018; 2011/0127222; 2011/0003303; 2010/0317093; and 2009/0053799, hereby incorporated herein by reference in their entirety for all purposes. Additional methods for concentrating and/or isolating CTC that can be applied to the present methods of concurrent isolation of CTC and stimulus-sensitive microparticles (e.g., thermolabile microspheres) are described, e.g., in Lin, et al., *Biosens Bioelectron.* 2012 Jun. 28., PMID 22784495; Yang, et al., *Technol Cancer Res Treat.* 2012 Jul. 10. PMID 22775338; O'Brien, et al., *J Biomed Opt.* (2012) 17(6): 061221, PMID 22734751; Hughes, et al., *J Vis Exp.* 2012 Jun. 15; (64). pii: 4248. doi: 10.3791/4248, PMID 22733259; Kim, et al., *Lab Chip.* 2012 Jun. 11, PMID 22684249; Yu, et al., *J Cell Biol.* (2011) 192(3):373-82; and Danova, et al., *Expert Rev Mol Diagn.* (2011) 11(5):473-85. Further applicable methods and systems of use in concentrating and/or isolating CTC are described, e.g., in U.S. Patent Publication Nos. 2012/0129252; 2012/0100560; 2012/0045828; and 2011/0059519.

The number of microparticles isolated or recovered from the mixture of cells is compared to the total number of microparticles that were spiked or mixed into the mixture of cells prior to processing. The percentage of microparticles isolated or recovered from the mixture of cells is representative of the efficiency of recovery of the cells of the rare cell population. Quantifying the number of microparticles input into and/or recovered from a mixture of cells can be done using any method in the art. In various embodiments, the number of microparticles input into and/or recovered from a mixture of cells is quantified by measuring the level of signal from the detectable label. The signal of the detectable label can be determined for each stimulus-sensitive microparticle (e.g., thermolabile microsphere) individually or for the microparticles as a group.

e. Subjecting the Isolated Microparticles and Isolated Cells in the Rare Cell Population to a Stimulus that Causes Dissolution and/or Degradation of the Microparticles After concurrent isolation of the cells of the rare cell population (e.g., CTCs) with the microparticles, the cells and the microparticles are exposed to a conditions sufficient to induce the dissolution and/or degradation of the microparticle. Such conditions include, e.g., exposure to a threshold temperature, a threshold pH, an enzyme, irradiaton or light. The threshold temperature and/or threshold pH or other stimulus that induces the dissolution and/or degradation of the microparticle will depend on the composition of the microparticle shell.

i. Threshold Temperature

In varying embodiments, the microparticles are temperature sensitive and degrade to release the one or more reporting molecules (e.g., target polynucleotide and/or detectable label) upon exposure to a threshold temperature.

Thermolabile microparticles can serve as a convenient measure of efficiency of genomic DNA recovery from cells of a rare cell population, particularly when the threshold temperature for degradation of the particle is approximately the temperature used to release genomic DNA from the cells. After isolation of the cells of the rare cell population (e.g., CTCs) with the thermolabile microparticles (e.g., thermolabile microspheres), genomic DNA is isolated from the cells and the one or more reporting molecules (e.g., target polynucleotide and/or detectable label) is isolated from the microparticles. Any method known in the art can be used for isolating the genomic DNA from the cells and the target polynucleotide from the microparticles. In order to release the one or more reporting molecules (e.g., target polynucleotide and/or detectable label) from the microparticles, the microparticles can be exposed to an elevated temperature of at least about 50° C. (e.g., at least about 55° C., 60° C., 65° C. or 70° C.) for a time period and under conditions sufficient for the thermolabile microparticle to degrade and release the one or more reporting molecules (e.g., target polynucleotide and/or detectable label). The higher the elevated temperature, the less exposure time of the microparticle to the elevated temperature conditions is required for the microparticle to degrade and release the target polynucleotide. For example, the thermolabile microparticles (e.g., thermolabile microspheres) comprising a polycaprolactone shell degrade in aqueous buffers when exposed to 55° C. for 3 hours or when exposed to 70° C. for 1 hour. Incubation of the cells and microparticles at an elevated temperature sufficient for the one or more reporting molecules (e.g., target polynucleotide and/or detectable label) to be released from the thermolabile microparticles or microspheres is oftentimes a part of the protocol for isolation of the genomic DNA from the cells, e.g., to inactive nucleases that degrade the genomic DNA.

Methods for purifying and/or isolating genomic DNA are well known in the art and can be applied in the present methods. Commercially available kits for purifying and/or isolating genomic DNA are readily available for purchase. Basic methodologies for purifying and/or isolating genomic DNA are described, e.g., in Green and Sambrook, *Molecular Cloning: A Laboratory Manual*, Fourth Edition, 2012, Cold Spring Harbor Laboratory Press; and Ausubel, et al., *Current Protocols in Molecular Biology*, Wiley, updated through Jul. 31, 2012. Kits of use for purifying and/or isolating genomic DNA can be purchased from numerous sources, including e.g., QIAGEN (on the internet at qiagen.com); Promega (on the internet at promega.com); Life Technologies (on the internet at invitrogen.com); G Biosciences (on the internet at gbiosciences.com); Sigma-Aldrich (on the internet at sigmaaldrich.com); Affymetrix (on the internet at affymetrix.com); and Fermentas Molecular Biology Tools (on the internet at fermentas.com).

f. Concurrently Amplifying and Quantifying the Genomic DNA from the Isolated Cells and the One or More Reporting Molecules Released from the Stimulus-Sensitive Microparticles After isolation of the genomic DNA from the cells of the rare cell population (e.g., CTCs) and the one or more reporting molecules (e.g., target polynucleotide and/or detectable label) released from the microparticles, the genomic DNA and one or more reporting molecules (e.g., target polynucleotide and/or detectable label) are quantified.

The recovered/isolated genomic DNA and the one or more reporting molecules (e.g., target polynucleotide and/or detectable label) can be quantified using any method known in the art. Methods for quantifying genomic DNA are well known in the art and can be applied in the present methods including quantifying target polynucleotide released from the microparticles. Commercially available kits and instrumentation for quantifying genomic DNA, e.g., by quantitative PCR, are readily available for purchase, e.g., from Roche Molecular Systems/Roche Applied Sciences, Thermoscientific Dharmacon, Sigma-Aldrich, Agilent Technologies. Basic methodologies for quantifying genomic DNA of use are described, e.g., in Green and Sambrook, *Molecular Cloning: A Laboratory Manual*, Fourth Edition, 2012, Cold Spring Harbor Laboratory Press; and Ausubel, et al., *Current Protocols in Molecular Biology*, Wiley, updated through Jul. 31, 2012; Waye, et al., *Biotechniques*. (1989) 7(8):852-5; Sestili, et al., *Mutation Research/Genetic Toxicology and Environmental Mutagenesis*, (2006) 607(2):205-214; Georgiou, et al., *Analytical Biochemistry* (2006) 358(2):247-256; Hague, et al., *BMC Biotechnology* (2003) 3:20. In some embodiments, the genomic DNA from the cells of the rare cell population (e.g., CTCs) and the target polynucleotide released from the microparticles are quantified using quantitative PCR (qPCR). Techniques for performing quantitative PCR are known in the art and can be applied in the present methods. Publications providing applicable protocols for performing quantitative PCR include, e.g., Bustin, "A-Z of Quantitative PCR (IUL Biotechnology, No. 5)," International University Line; (2004); "Quantitative PCR Protocols (Methods in Molecular Medicine)" Kochanowski and Reischl, editors, Humana Press; (1999); "Quantitative Real-time PCR in Applied Microbiology," Martin Filion (Editor), Caister Academic Press (2012); and Arya, et al., *Expert Rev Mol Diagn*. 2005 Mar. 5(2):209-19.

The quantity and quality of target polynucleotide isolated or recovered from the recovered microparticles is compared to the quantity and quality of the target polynucleotide of a predetermined number of control microparticles that were not mixed into the biological sample. The quantity and quality of the target polynucleotide isolated or recovered from the recovered microparticles is representative of the quantity and quality of the genomic DNA recovered from the cells of the rare cell population (e.g., CTCs).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A thermolabile microsphere comprising:
   i) a thermolabile homopolymer comprising an inner space and an external surface, wherein the homopolymer contains a target nucleic acid in the inner space, wherein the homopolymer transitions from a crystalline or semi-crystalline phase to a liquid/melt/flow phase over 10 or fewer ° C. and releases the nucleic acid at a temperature above about 60° C., wherein the homopolymer comprises polycaprolactone (PCL) monomers, the PCL monomers comprising a molecular weight in the range of about Mn 10,000 to about Mn 90,000, where Mn refers to number average molar mass; and
   ii) a surface capture antigen or ligand attached to an external surface of the homopolymer.

2. The microsphere of claim 1, wherein the microsphere further comprises:
   iii) a detectable label being detectable while contained within the inner space of the thermolabile microsphere.

3. The microsphere of claim 1, wherein the microsphere has a size in the range of about 10-30 μm.

4. The microsphere of claim 1, wherein the microsphere has a size in the range of about 20-30 μm.

5. The microsphere of claim 1, wherein the target nucleic acid comprises DNA.

6. The microsphere of claim 1, wherein the target nucleic acid is comprised in a DNA plasmid.

7. The microsphere of claim 1, wherein the target nucleic acid encodes a non-human DNA sequence, a mutated human DNA sequence or an artificial DNA sequence.

8. The microsphere of claim 1, wherein the surface capture antigen or ligand is selected from Epithelial cell adhesion molecule (Ep-CAM) and digoxigenin.

9. The microsphere of claim 2, wherein the detectable label is a fluorophore.

10. The microsphere of claim 9, wherein the fluorophore comprises an excitation peak at about 460 nm and an emission peak at about 500 nm.

11. A method of tracking the efficiency of recovery of a rare cell population from a mixture of cells, comprising:
   a) mixing a predetermined number of thermolabile microspheres of claim 1 with a mixture of cells suspected of comprising a cell of a rare cell population, wherein the thermolabile microspheres comprise:
      (i) a thermolabile polymer comprising an inner space and an external surface, wherein the polymer contains a target nucleic acid in the inner space, wherein the polymer transitions from a crystalline or semi-crystalline phase to a liquid/melt/flow phase over 10 or fewer ° C. and releases the nucleic acid at a temperature above about 50° C., wherein the polymer is selected from the group consisting of polycaprolactone (PCL), polymethyl methacrylate (PMMA) and Poly Lactic-co-Glycolic Acid (PLGA); and
      (ii) a surface capture antigen or ligand attached to an external surface of the polymer,
   wherein the surface capture antigen or ligand attached to the external surface of microsphere is the same epitope used to isolate the rare cell population;
   b) adding to the mixture of cells comprising the thermolabile microspheres a binding partner that binds to the surface capture antigen or ligand;
   c) concurrently isolating binding partner-bound microspheres and cells of the rare cell population from the mixture of cells, wherein the number of microspheres captured is representative of the efficiency of capture of cells in the rare cell population from the mixture of cells;
   d) subjecting the isolated microspheres and isolated cells in the rare cell population to a temperature of at least 50° C., under conditions that concurrently release genomic DNA from the cells and release the target nucleic acid from the microsphere; and
   e) concurrently amplifying and quantifying the genomic DNA from the isolated cells and the target nucleic acid released from the thermolabile microspheres, wherein the quantity of target nucleic acid amplified is representative of the efficiency of recovery of genomic DNA from the isolated cells of the rare cell population, thereby tracking the efficiency of recovery of the rare cell population from the mixture of cells.

12. The microsphere of claim 1, wherein the PCL monomers comprise a molecular weight in the range of about Mn 70,000 to about Mn 90,000.

13. The microsphere of claim 1, wherein the surface capture antigen or ligand is a circulating tumor cell (CTC)-associated marker selected from the group consisting of Epithelial cell adhesion molecule (Ep-CAM), mucin 1 (MUC1), carcinoembryonic antigen-related cell adhesion molecule 5 (CEACAM5), and ERBB2.

14. The microsphere of claim 1, wherein the target nucleic acid encodes a protein selected from plasmid maintenance protein (ccdB) and 3',5'-cyclic adenosine monophosphate phosphodiesterase cpdA.

15. The method of claim 11, further comprising:
prior to d), identifying a number of microspheres isolated during c) by interrogating the detectable label; and
comparing the identified number of microspheres with the predetermined number provided in a).

16. The method of claim 11, wherein the rare cell population comprises circulating tumor cells (CTC).

17. The method of claim 11, wherein the mixture of cells is in a biological sample from a patient.

18. The method of claim 11, wherein the biological sample is whole blood.

19. The method of claim 11, wherein the predetermined number of thermolabile microspheres is in the range of about 10 to about 100 microspheres.

20. The method of claim 11, wherein the patient is a human.

21. The method of claim 11, wherein the binding partner that binds to the surface capture antigen or ligand is an antibody or antibody fragment.

22. A thermolabile microsphere comprising:
i) a thermolabile homopolymer comprising an inner space and an external surface, wherein the homopolymer contains a target nucleic acid in the inner space, wherein the homopolymer transitions from a crystalline or semi-crystalline phase to a liquid/melt/flow phase over 10 or fewer ° C. and releases the nucleic acid at a temperature above about 50° C., wherein the homopolymer is polycaprolactone (PCL); and
ii) a surface capture antigen or ligand attached to an external surface of the homopolymer, wherein the surface capture antigen or ligand is selected from the group consisting of Epithelial cell adhesion molecule (Ep-CAM), digoxigenin, mucin 1 (MUC1), carcinoembryonic antigen-related cell adhesion molecule 5 (CEACAM5), and ERBB2.

23. A thermolabile microsphere comprising:
i) a thermolabile polymer comprising an inner space and an external surface, wherein the polymer contains a target nucleic acid in the inner space, wherein the polymer transitions from a crystalline or semi-crystalline phase to a liquid/melt/flow phase over 10 or fewer ° C. and releases the nucleic acid at a temperature above about 50° C., wherein the polymer is selected from the group consisting of polycaprolactone (PCL), polymethyl methacrylate (PMMA) and Poly Lactic-co-Glycolic Acid (PLGA); and
ii) a surface capture antigen or ligand attached to an external surface of the polymer, wherein the surface capture antigen or ligand is selected from the group consisting of Epithelial cell adhesion molecule (Ep-CAM), digoxigenin, mucin 1 (MUC1), carcinoembryonic antigen-related cell adhesion molecule 5 (CEACAM5), and ERBB2.

24. A method of tracking the efficiency of recovery of a rare cell population from a mixture of cells, comprising:
a) mixing a predetermined number of thermolabile microspheres with a mixture of cells suspected of comprising a cell of a rare cell population, wherein the thermolabile microspheres comprise
(i) a thermolabile polymer comprising an inner space and an external surface, wherein the polymer contains a target nucleic acid in the inner space, wherein the polymer transitions from a crystalline or semi-crystalline phase to a liquid/melt/flow phase over 10 or fewer ° C. and releases the nucleic acid at a temperature above about 50° C., wherein the polymer is selected from the group consisting of polycaprolactone (PCL), polymethyl methacrylate (PMMA) and Poly Lactic-co-Glycolic Acid (PLGA); and
(ii) a surface capture antigen or ligand attached to an external surface of the polymer, wherein the surface capture antigen or ligand is selected from the group consisting of Epithelial cell adhesion molecule (Ep-CAM), digoxigenin, mucin 1 (MUC1), carcinoembryonic antigen-related cell adhesion molecule 5 (CEACAM5), and ERBB2;
wherein the surface capture antigen or ligand attached to the external surface of microsphere is the same epitope used to isolate the rare cell population;
b) adding to the mixture of cells comprising the thermolabile microspheres a binding partner that binds to the surface capture antigen or ligand;
c) concurrently isolating binding partner-bound microspheres and cells of the rare cell population from the mixture of cells, wherein the number of microspheres captured is representative of the efficiency of capture of cells in the rare cell population from the mixture of cells;
d) subjecting the isolated microspheres and isolated cells in the rare cell population to a temperature of at least 50° C., under conditions that concurrently release genomic DNA from the cells and release the target nucleic acid from the microsphere; and
e) concurrently amplifying and quantifying the genomic DNA from the isolated cells and the target nucleic acid released from the thermolabile microspheres, wherein the quantity of target nucleic acid amplified is representative of the efficiency of recovery of genomic DNA from the isolated cells of the rare cell population, thereby tracking the efficiency of recovery of the rare cell population from the mixture of cells.

25. The microsphere of claim 1, wherein the PCL monomers comprise a molecular weight in the range of about Mn 10,000 to about Mn 14,000.

* * * * *